US00PP37107P2

(12) United States Plant Patent
Dirr et al.

(10) Patent No.: US PP37,107 P2
(45) Date of Patent: Nov. 25, 2025

(54) ***HYDRANGEA* PLANT NAMED 'RNR X AS-01-22'**

(50) Latin Name: *Hydrangea macrophylla*
Varietal Denomination: RNR X AS-01-22

(71) Applicant: Premier Introductions Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 19/185,916

(22) Filed: Apr. 22, 2025

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
CPC ..... A01H 6/48; A01H 5/02
See application file for complete search history.

*Primary Examiner* — Keith O. Robinson

(57) ABSTRACT

A new and distinct cultivar of *Hydrangea macrophylla* plant named 'RnR x AS-01-22', characterized by its glossy dark green foliage with red petioles, remontant (reblooming) trait, flowering on old wood and new growth of the season, pink mophead inflorescence in non-aluminium based media and blue inflorescence in aluminum based media, foliar *Cercospora* resistance, and its compact, rounded to spreading habit. The new cultivar is a *Hydrangea*, typically produced as an outdoor ornamental plant.

6 Drawing Sheets

Latin name of the genus and species: *Hydrangea macrophylla.*

Variety denomination: 'RNR X AS-01-22'.

BACKGROUND OF THE INVENTION

The present invention relates to a new and distinct cultivar of *Hydrangea macrophylla*, a member of the Hydrangeaceae family, hereinafter referred to by its cultivar name 'RNR X AS-01-22'. This cultivar is grown primarily as an ornamental for landscape use and for use as a potted plant. The cultivar originated from an open pollination of *Hydrangea macrophylla* 'COF-14 HM3', U.S. Plant Pat. No. 32,584, as the female parent by *Hydrangea macrophylla* 'COF-HM1', U.S. Plant Pat. No. 32,054, as the male parent in Watkinsville, Georgia, in 2021, and was selected from the progeny by continued evaluation for growth habit, floral, and foliage characteristics.

'RNR X AS-01-22' has been asexually reproduced by softwood cuttings since 2022 in Watkinsville, Georgia. The characteristics of the cultivar have been stable and reproduced true to type in successive vegetative generations.

SUMMARY OF THE INVENTION

'RNR X AS-01-22' has not been observed under all possible environmental conditions. The phenotype may vary somewhat with changes in light, temperature, soil and rainfall without, however, any variance in genotype.

The following traits have been repeatedly observed and are determined to be the unique characteristics of 'RNR X AS-01-22'. These characteristics in combination distinguish 'RNR X AS-01-22' as a new and distinct *Hydrangea* cultivar:

1. Dark-green foliage with high mildew and Cercospora resistances.

2. Remontant (reblooming) trait, flowering on old wood and new growth of the season.
3. Pink mophead inflorescence in non-aluminum-based media and blue inflorescence in aluminum-based media.
4. Compact, rounded to spreading growth habit.

PARENT COMPARISONS

Plants of the new cultivar *Hydrangea* 'RNR X AS-01-22' can be compared to the seed parent variety in most horticultural characteristics, however, plants of 'RNR X AS-01-22' differ in the following:

1. 'RNR X AS-01-22' has a true blue, uniform flower color compared with 'COF-HM3'.
2. 'RNR X AS-01-22' is more compact than 'COF-HM3'.
3. Plants of 'RNR X AS-01-22' flower more prolifically than plants of 'COF-HM3'.

Plants of the new cultivar *Hydrangea* 'RNR X AS-01-22' can be compared to the pollen parent variety in most horticultural characteristics, however, plants of 'RNR X AS-01-22' differ in the following:

1. Plants of 'RNR X AS-01-22' are hardier and more compact than plants of 'COF-HM1'.
2. Plants of 'RNR X AS-01-22' flower more prolifically than plants of 'COF-HM1'.
3. Plants of 'RNR X AS-01-22' have better resistance to Cercospora and mildew than plants of 'COF-HM1'.

COMMERCIAL COMPARISON

Plants of the new cultivar *Hydrangea* 'RNR X AS-01-22' can be compared to the commercial variety *Hydrangea* 'Bailmer', U.S. Plant Pat. No. 15,298. Plants of 'RNR X AS-01-22' are similar to plants of 'Bailmer' in most horticultural characteristics, however, plants of 'RNR X AS-01-22' differ in the following:

1. Foliage color of 'RNR X AS-01-22' is darker green than the foliage color of this comparator.
2. Plants of 'RNR X AS-01-22' flower more prolifically than plants of this comparator.
3. Plants of 'RNR X AS-01-22' are more compact than plants of this comparator.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea*. Plants were grown in Watkinsville, GA.

FIG. 1: Shows 'RNR X AS-01-22', a two-year-old plant, grown in containers with pink and blue blooms.

FIG. 2: Shows a 2-year-old 'RNR X AS-01-22' flower grown with aluminum.

FIG. 3: Shows a group of young 'RNR X AS-01-22' plants developing numerous flower buds on new growth, grown without aluminum at about 6 months of age.

Figure 1:
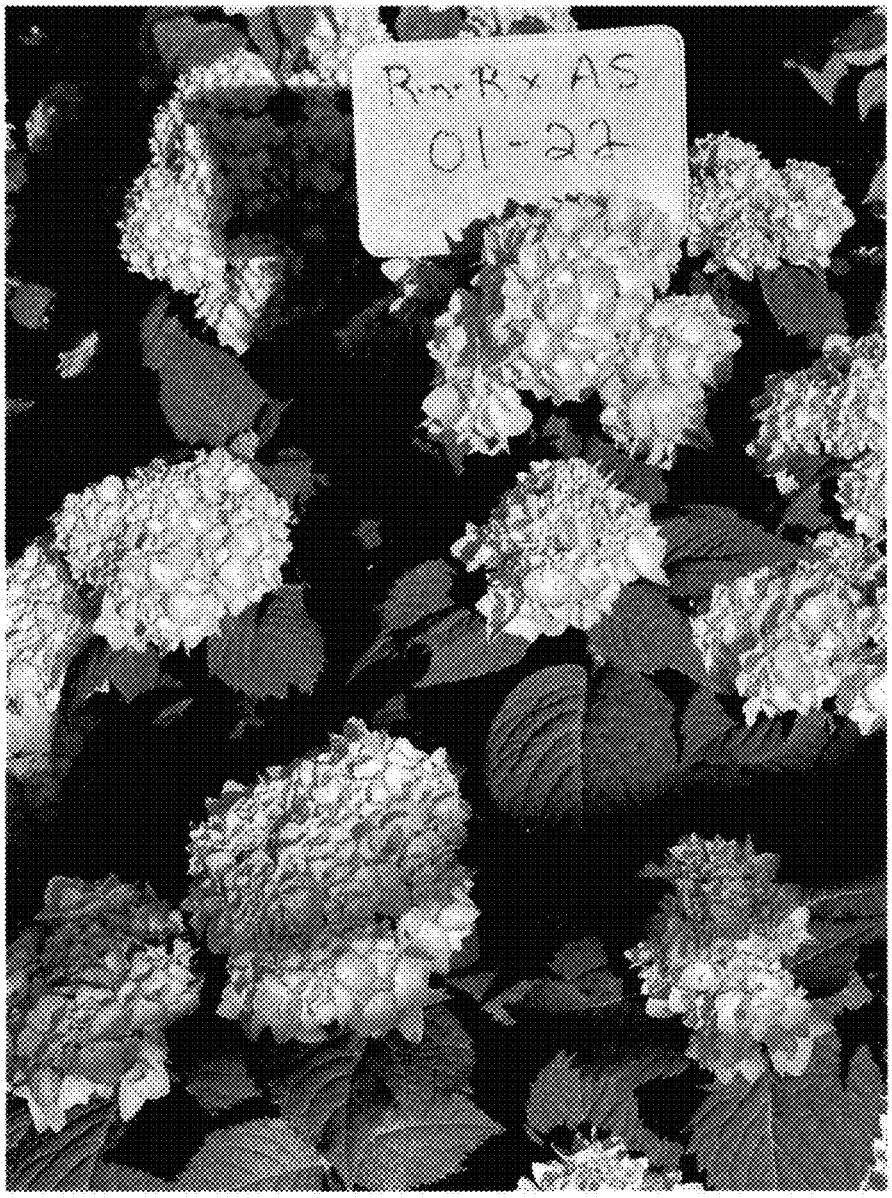
Figure 2:
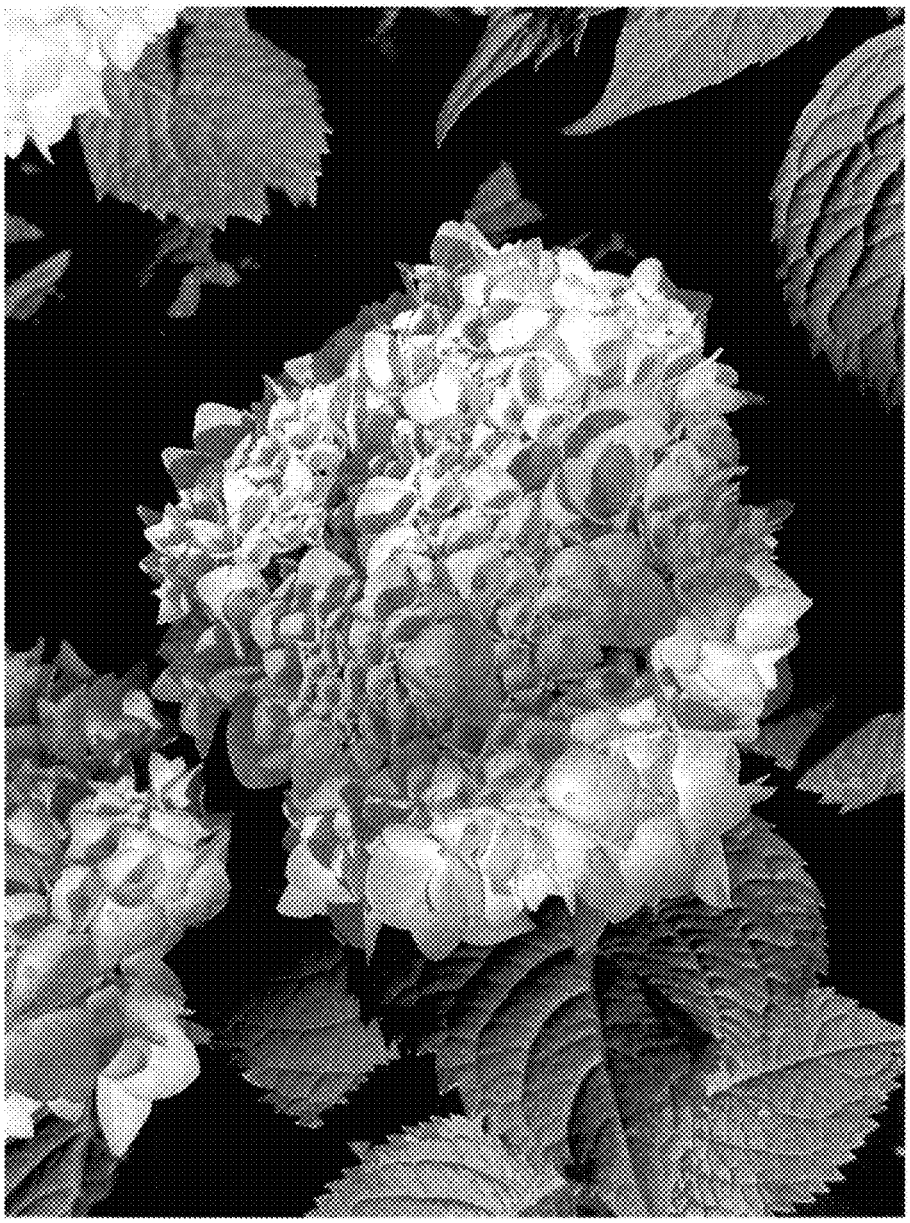
Figure 3:
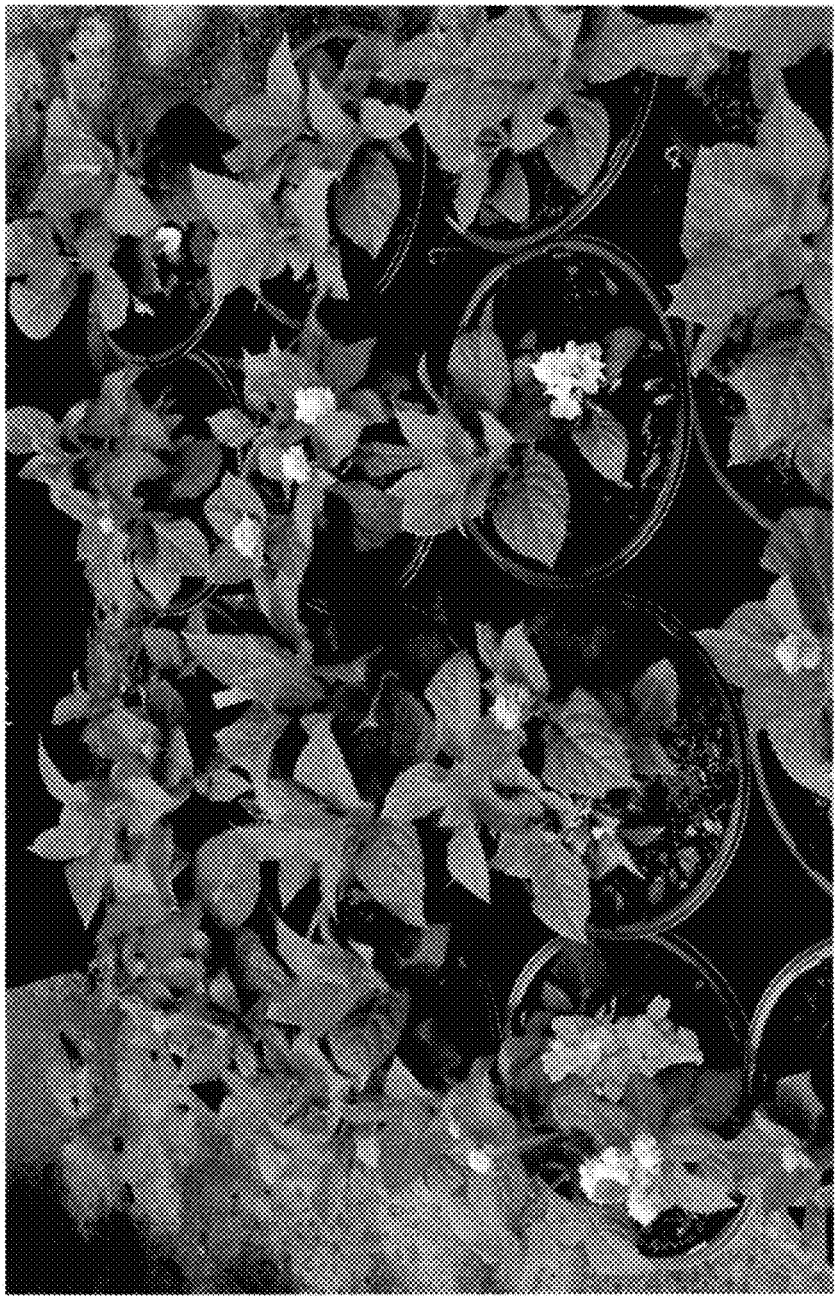
Figure 4:
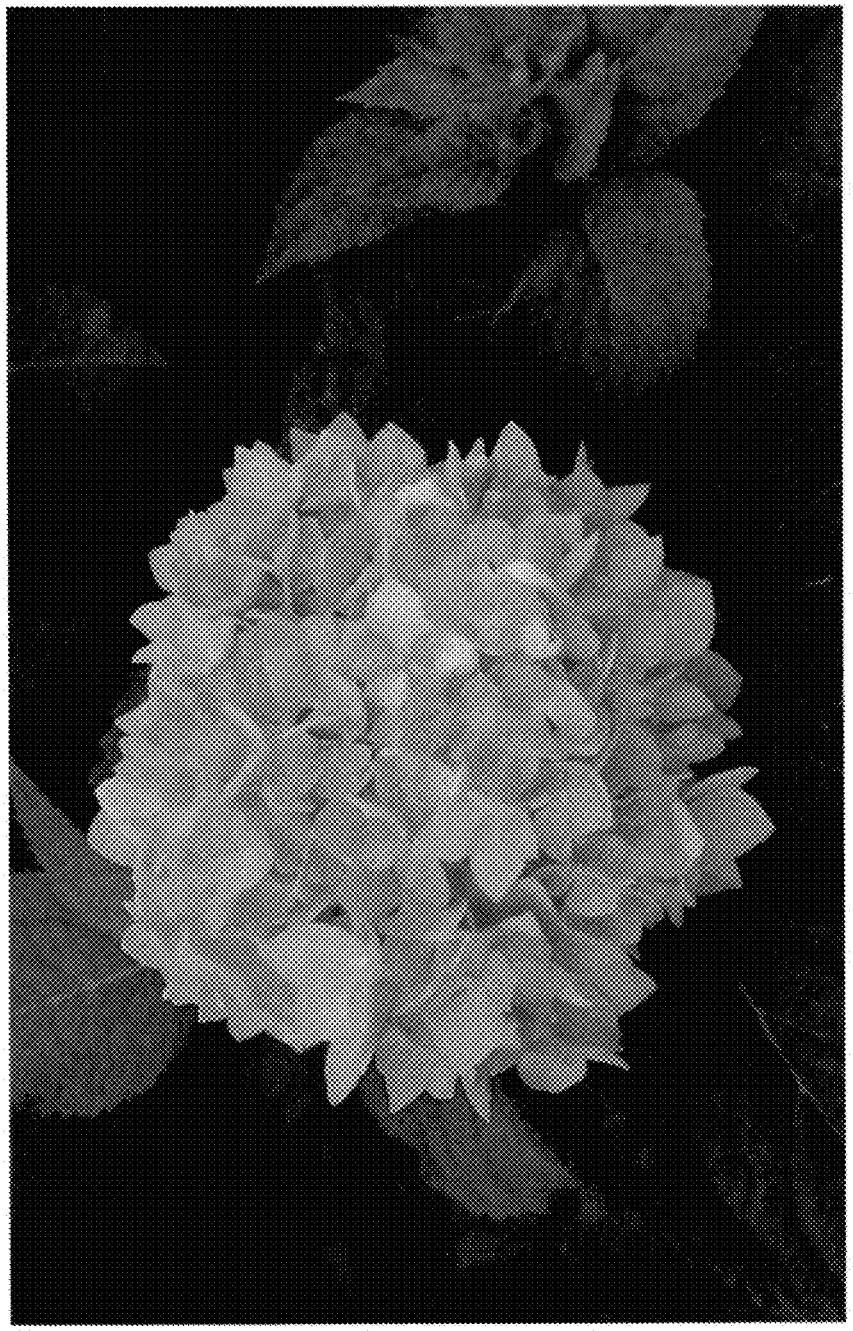
FIG. 4 shows a young plant flower of 'RNR X AS-01-22' grown without aluminum from a plant of about 18 months old.
Figure 5:
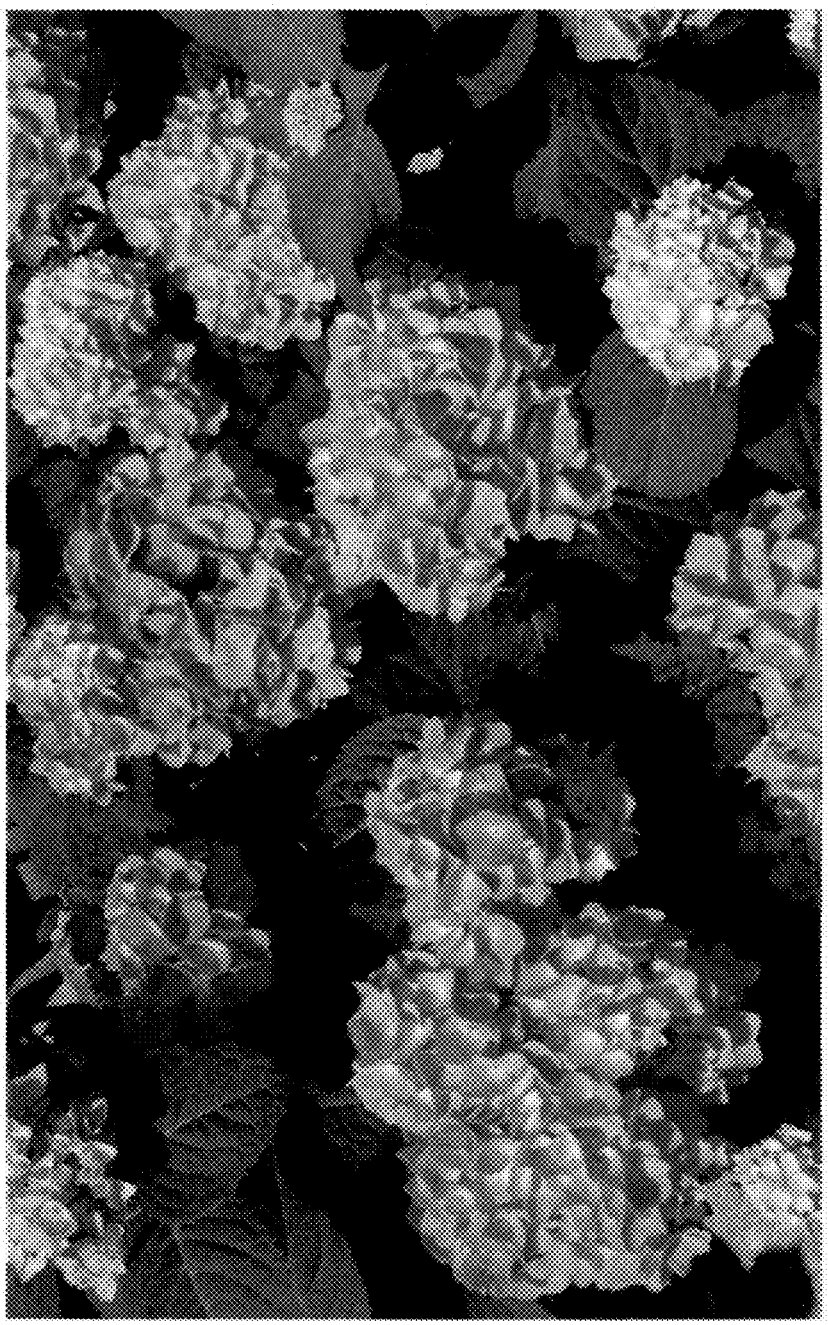
FIG. 5 shows inflorescences on a flowering plant of 'RNR X AS-01-22' grown with aluminum. The plant producing these inflorescences is about 2 year old.
Figure 6:
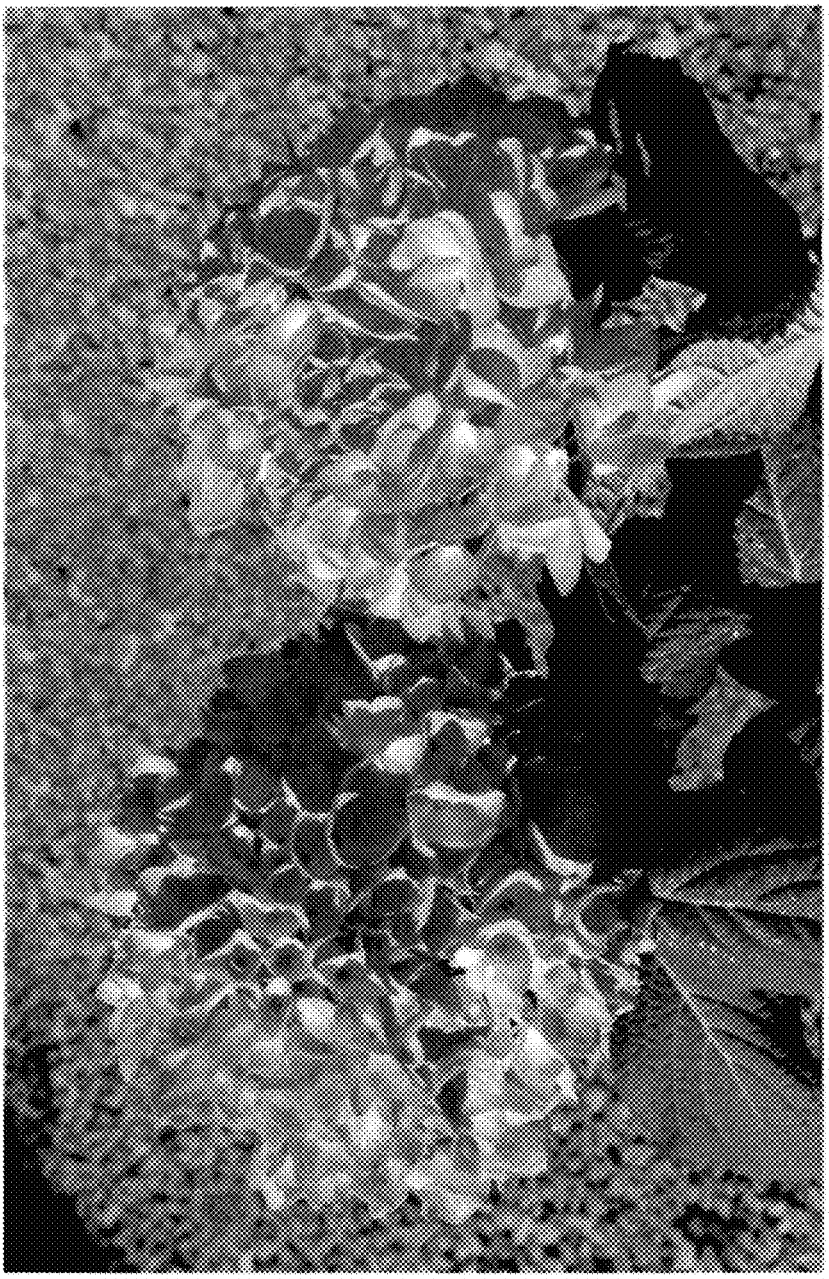

FIG. 6 is a comparison of inflorescences of 'RNR X AS-01-22'. The inflorescence on the left of the photograph were grown with aluminum. The inflorescence on the right was not given aluminum treatment. The plants producing these inflorescences are about 2 year old.

DETAILED BOTANICAL DESCRIPTION

In the following description, color references are made to The Royal Horticultural Society Colour Chart, 2015 Edition, except where general terms of ordinary dictionary significance are used. Plants used for the description were grown in 26.5 L containers under 50% shade under outdoor conditions in a nursery in Watkinsville, GA. Plants were about two years old when the description was recorded. Two groups of plants were used for the description to describe the flower colors with and without aluminum. The first group was grown in a medium consisting of composted pine bark, with no aluminum present and a pH of 5.4. The second group was grown in a medium consisting of composted pine bark that was amended with 60 grams of aluminum sulphate and a pH of 5.3. Aluminum only affects flower color. Therefore, colors with and without aluminum are only specified for floral parts.

Botanical classification: *Hydrangea macrophylla* 'RNR X AS-01-22'.

PROPAGATION

Typical method: Vegetatively by stem cuttings.

Root initiation: Approximately 14 days at 32° C.

Time to produce rooted cutting: About 3 months at 32° C. during summer.

Time to produce a finished crop: In a 11.4 L container potted with a 0.041 L liner pot, about 9 months.

Roots: Root description: numerous, fine, fibrous and well-branched. Color: RHS White NN155A.

PLANT

Plant type: Rounded and spreading deciduous shrub.

Height: 29 cm.

Plant spread: 53 cm.

Age of plant described: Approximately 2 years.

Branching characteristics: Freely-branching. Pinching enhances branching.

Number of lateral branches: About 8 per plant.

First year stems:

*Length*.—19 cm.
*Width*.—4 mm.
*Color*.—RHS Yellow-Green 144A.
*Shape*.—Round.
*Strength*.—Flexible.
*Texture*.—Smooth.

Second year stems:

*Length*.—35 cm.
*Width*.—6 mm.
*Color*.—RHS Brown 199C.
*Shape*.—Round.
*Strength*.—Easily broken.
*Texture*.—Woody.

Lenticels:

*Quantity*.—20 to 30 per internode; 4 internodes per stem.
*Color*.—RHS Brown 165A on old and new growth.

Vegetative buds:

*Arrangement*.—Opposite.
*Shape*.—Ovoid.
*Length*.—2 mm.
*Width*.—1 mm.
*Color*.—RHS Yellow-Green 144A.

FOLIAGE

Leaf:

*Arrangement*.—Opposite, simple.
*Shape*.—Ovate.
*Length*.—12 cm.
*Width*.—8 cm.
*Apex*.—Acuminate.
*Base*.—Cuneate.
*Margin*.—Serrate.
*Texture of top surface*.—Glabrous.
*Texture of bottom surface*.—Glaucescent.
*Color*.—Young foliage upper side: RHS Yellow-Green 143B. Young foliage under side: RHS Yellow-Green 144B. Mature foliage upper side: RHS Green N137B. Mature foliage, under side: RHS Green 138B.

Venation:

*Type*.—Pinnate.
*Color*.—Young, upper side: RHS Yellow-Green 143C. Young, under side: RHS Green 139D. Mature, upper side: RHS Yellow-Green 143C. Mature, under side: RHS Green 139D.

Petiole:
*Length.*—1 cm.
*Width.*—3 mm.
*Color.*—Upper side: RHS Yellow-Green 145A. Under side: RHS Yellow-Green 145A.
*Texture.*—Smooth, glabrous. Petiole is grooved on upper side, and crescent-shaped in cross section.

INFLORESCENCE

Natural flowering season: Early summer to mid-frost in fall. The inflorescence is effective for about 8 weeks.
Inflorescence type: Mophead.
*Height.*—8 cm.
*Diameter.*—17 cm.
*Shape.*—Globular.
Fragrance: None.
Bud:
*Bud length.*—6 mm.
*Bud diameter.*—4 mm.
*Bud shape.*—Ovoid.
*Bud color.*—Prior to opening: RHS Yellow-Green 145B. When opening, with aluminum: RHS Purplish-Blue 100C. When opening, without aluminum: RHS Purple 73D.
Sterile florets:
*Flowers per inflorescence.*—About 250.
*Shape.*—Ovoid.
*Tip.*—Obtuse.
*Base.*—Acute.
*Margin.*—Entire.
*Diameter.*—3 cm.
Sepals:
*Number per Flower.*—4.
*Length.*—2 cm.
*Width.*—1.5 cm.
*Texture.*—Upper side: Smooth. Under side: Smooth.
*Color.*—At maturity, with aluminum: Upper side: RHS Blue 98B. Under side: RHS Purplish-Blue 97C. At maturity, without aluminum: Upper side: RHS Purplish-Pink 73C. Under side: RHS Purplish-Pink 73D. Aged sepals, with aluminum: Upper side: RHS Purplish-Blue 98D. Under side: RHS Purplish-Blue 97C. Aged sepals, without aluminum: Upper side: RHS Purple 69B. Under side: RHS Purple 69C.
Fertile flowers:
*Flowers per inflorescence.*—About 47.
Petals:
*Number per flower.*—5.
*Shape.*—Ovate.
*Tip.*—Acuminate.
*Base.*—Truncate.
*Margin.*—Entire.
*Length.*—3 mm.
*Width.*—1.5 mm.
*Texture.*—Smooth, no pubescence.
*Color.*—With aluminum, upper side: RHS Purplish-Blue 94B. With aluminum, under side: RHS Purplish-Blue 94C. Without aluminum, upper side: RHS Red-Purple N74D. Without aluminum, under side: RHS Purple 75D.
Peduncle:
*Length.*—2 cm.
*Diameter.*—4 mm.
*Angle.*—Upright.
*Strength.*—Moderately strong and flexible.
*Color.*—RHS Yellow-Green 144B.
Pedicel:
*Length.*—1 cm.
*Diameter.*—1 mm.
Angle.—45° from vertical.
*Strength.*—Moderately strong and flexible.
*Texture.*—Smooth.
*Color.*—With aluminum: RHS Purplish-Blue 98C. Without aluminum: RHS Yellow-Green 157A.

REPRODUCTIVE ORGANS

Stamens:
*Number.*—4 to 5 per flower.
*Filament length.*—3 mm.
*Filament color.*—With aluminum: RHS Purplish-Blue 94B. Without aluminum: RHS Purplish-Pink 62C.
Anthers:
*Length.*—About 1 mm.
*Width.*—0.5 mm.
*Color.*—With aluminum: RHS Purplish-Blue 94B. Without aluminum: RHS Purplish-Pink 62D.
*Pollen amount.*—Moderate.
*Pollen color.*—RHS Yellow-White 155A.
Pistil:
*Number.*—1.
*Length.*—3 mm.
*Width.*—1.5 mm.
*Color.*—With aluminum: RHS Purplish-Blue 94B. Without aluminum: RHS Purple-Red 63B.
Stigma:
*Number.*—2 or 3.
*Shape.*—Round.
*Color.*—With aluminum: RHS Purplish-Blue 94A. Without aluminum: RHS Purple 85B.
*Style length.*—2 mm.
*Style shape.*—Tubular.
*Style color.*—With aluminum: RHS Purplish-Blue 94A. Without aluminum: RHS Purple 85D.

OTHER CHARACTERISTICS

Fruit:
*Number.*—Average range 40 to 65 per infructescence.
*Shape.*—Ovoid.
*Length.*—3 mm.
*Width.*—2 mm.
*Color.*—During ripening: Near RHS Purplish-Pink 54B. At maturity: Near RHS Brown 200C.
Seeds:
*Number.*—About 25 seeds per capsule.
*Shape.*—Round.
*Length.*—0.5 mm.
*Width.*—0.5 mm.
*Color.*—Near RHS Brown 199B.
Disease resistance: High *Cercospora* and mildew resistance. The specific mildew pathogens have not been identified. Typical pathogens causing mildew in *Hydrangea* include *Golovinocyces orontii, Erysiphe poeltii, Microsphaera friesii* and *Odium hortensiae*. Susceptibility or resistance to diseases beyond that typically found in other *Hydrangea macrophylla* plants has not been observed.
Drought tolerance and cold tolerance: USDA Hardiness Zone Map (2012): Zones 5-9.

What is claimed is:

1. A new and distinct cultivar of *Hydrangea* plant named 'RnR x AS-01-22' as herein illustrated and described.

* * * * *